(12) United States Patent
Hettwer et al.

(10) Patent No.: US 6,708,554 B2
(45) Date of Patent: Mar. 23, 2004

(54) ROTATIONAL RHEOMETER

(75) Inventors: Dirk Hettwer, Karlsruhe (DE); Wolfgang Platzek, Karlsruhe (DE)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 0 days.

(21) Appl. No.: 10/252,505

(22) Filed: Sep. 24, 2002

(65) Prior Publication Data

US 2003/0056575 A1 Mar. 27, 2003

(30) Foreign Application Priority Data

Sep. 25, 2001 (DE) .......................................... 101 47 200

(51) Int. Cl.[7] .............................................. G01N 11/00
(52) U.S. Cl. ..................... 73/54.43; 73/54.38; 73/54.28
(58) Field of Search .............................. 73/54.43, 54.38, 73/54.29, 54.28, 54.3, 54.31, 54.32, 54.33, 54.34, 54.35

(56) References Cited

U.S. PATENT DOCUMENTS

| 2,491,639 | A | * | 12/1949 | Bechtel et al. | ............. | 73/54.32 |
|---|---|---|---|---|---|---|
| 2,703,006 | A | * | 3/1955 | Savins | ........................ | 73/54.33 |
| 2,869,358 | A | * | 1/1959 | Heisig | ........................ | 73/54.34 |
| 3,465,575 | A | * | 9/1969 | Kepes | ........................ | 73/54.32 |
| 3,935,726 | A | * | 2/1976 | Heinz | ........................ | 73/54.35 |
| 4,095,461 | A | | 6/1978 | Starita | | |
| 4,445,365 | A | * | 5/1984 | Selby | ........................ | 73/54.34 |
| 4,736,593 | A | * | 4/1988 | Williams | .................... | 73/54.32 |
| 5,481,903 | A | | 1/1996 | King | | |
| 6,240,770 | B1 | * | 6/2001 | Raffer | ........................ | 73/54.28 |

FOREIGN PATENT DOCUMENTS

| DE | 23 65 538 | 11/1975 |
|---|---|---|
| DE | 199 11 441 | 9/2000 |
| DE | 100 58 399 | 5/2001 |
| EP | 0 136 994 | 4/1985 |

* cited by examiner

*Primary Examiner*—Michael Cygan
(74) *Attorney, Agent, or Firm*—Paul Vincent

(57) ABSTRACT

A rotational rheometer has a cylindrical outer housing into which a measuring container can be inserted substantially coaxially thereby forming a radial annular space. The measuring container has a measuring chamber for receiving a sample material. A fluid may flow through the annular space to bring the outside of the measuring container and thereby the sample material to a desired temperature. The fluid is a gas and a circulating device is provided within the outer housing for circulating the gas.

11 Claims, 3 Drawing Sheets

ROTATIONAL RHEOMETER

This application claims Paris Convention priority of DE 101 47 200.5 filed Sep. 25, 2001 the complete disclosure of which is hereby incorporated by reference.

BACKGROUND OF THE INVENTION

The invention concerns a rotational rheometer comprising a cylindrical outer housing which is seated on a support and into which a measuring container can be inserted substantially coaxially to thereby form a radial annular space, the measuring container having a measuring chamber for receiving a sample material, wherein a fluid can flow through the annular space to temperature-control the outside of the measuring container, and therefore the sample material, to a required temperature.

Measurement of rheological values in a rotational rheometer is based on the exact knowledge of the relation between shearing strain $\tau$ and deformation $\gamma$ of a sample. In order to derive the material properties from these values, the shearing strain and deformation of the sample must be measured as precisely as possible. One therefore strives to measure both values in a region in which disturbing background effects are small, i.e. where the signal/noise ratio is as large as possible. It is often very difficult, in particular with low viscosity samples, to obtain suitable measuring values since relatively large deformations produce only small shearing strain. To solve this problem, the measuring surface is conventionally enlarged, since the shearing strain depends on the size of the measuring surface.

To increase the measuring surface, the sample is conventionally caused to flow in a laminar fashion through an annular space formed between two coaxial circular cylinders. Since the rheological properties of a sample usually depend strongly on the material temperature or ambient temperature, to obtain distinctive measuring results, the sample material must be precisely controlled to a predetermined temperature. For an apparatus with the above-mentioned geometry, this is usually achieved in that the outer of the two circular cylinders, i.e. the so-called measuring container, is stationary and has an outer temperature-controlling device. The temperature-controlling device should maintain the measuring container and therefore the sample material located therein, at a desired temperature.

Conventional temperature-controlling devices have differing structures. The outside of the measuring container, which is usually made from metal, can be provided with a heating wire which can heat the outer surface of the measuring container. Since the metallic measuring container has good thermal conducting properties, the sample material can also be brought to and maintained at a desired temperature value with great accuracy. However, the container is disadvantageously subjected to strict constraints when the geometrical shape of the measuring chamber changes, i.e. when the gap width and/or the measuring surface are thereby changed, since the outside wall of the measuring container must stay in contact with the heating wire. To change the measuring chamber geometry, another measuring container with identical outer dimensions but different inner dimensions and wall thicknesses must be used. Determination of the sample material temperature is therefore problematic, since the temperature is measured on the outside wall of the container and different measuring containers produce different temperatures in the sample material in dependence on their differing wall thicknesses. Therefore, the wall thickness differences of different measuring containers are highly disadvantageous from a control technology standpoint.

Alternatively, the outside of the measuring container is introduced into a liquid bath. The liquid which is water, glycol or, particularly at high temperatures, oil is introduced into the inside of the outer housing and brought to and maintained at a desired temperature using a temperature-controlling device. The good thermal conductivity of the liquid produces rapid and homogeneous temperature adjustment. At the same time, the wall thickness of the measuring container, which is surrounded by the liquid, can be reduced which improves thermal transfer to the sample material. Since the liquid adjusts to any outer contour of the measuring container, different measuring containers of identical wall thicknesses can be used for different measuring chamber geometries. This is advantageous in that the temperature difference which occurs between liquid on the outside wall of the measuring container and the inner sample material does not change with the measuring chamber geometry. Moreover, the temperature can be detected at any point within the liquid and not necessarily directly on the outside wall of the measuring container. However, such a rotational rheometer is disadvantageous in that the oil is difficult to handle and produces unpleasant odors during heating. Moreover, the liquid can leak and render the rotational rheometer useless.

It is therefore the underlying purpose of the invention to produce a rotational rheometer which eliminates the above-mentioned disadvantages and which guarantees rapid and precise temperature-control of the sample material, irrespective of the geometry of the measuring chamber.

SUMMARY OF THE INVENTION

This object is achieved in accordance with the invention with a rotational rheometer having features characterizing the independent claim. It uses gas, preferably air, as the temperature-controlling or thermal transfer medium and not liquid. The oils which are used for conventional rotational rheometers have very good thermal conducting properties and react quickly to temperature changes resulting in a homogeneous temperature distribution within the oil and uniform and precise heating of the measuring container within a short period of time. Gases, in particular air, have considerably worse thermal conducting properties. As a result large, unwanted temperature variations may occur within the air. To compensate for this disadvantage, the invention provides for a circulation device which circulates the gas within the annular chamber. Permanent mixing of the gas produces a uniform temperature distribution throughout the entire volume and thereby uniform and precise heating of the measuring container and of the sample.

In a preferred embodiment of the invention, the circulating device comprises a propeller with rotational drive which keeps the air in constant motion.

The gas or the air is preferably circulated in a directed manner within the annular space. This can be realized e.g. by providing a cylindrical guiding wall in the annular space which extends at a separation from and coaxially to the outer housing and which divides the annular space into an inner annular chamber and an outer annular chamber. The inside of the inner annular chamber is defined by the outside of the inserted measuring container and its outside by the inside of the guiding wall. The inside of the outer annular chamber is defined by the outside of the guiding wall and the outside thereof by the inside of the outer housing. The outer annular chamber and the inner annular chamber are interconnected via at least one opening in the guiding wall.

In a further development of the invention, the guiding wall has a substantially horizontal bottom below the measuring container which has at least one opening. The propeller may be disposed below the bottom and initially forces the air radially outwardly which then rises in the outer annular chamber. The air passes through the openings which are formed in the upper region of the guiding wall and into the inner annular chamber and flows therein back towards the bottom and through the bottom opening back to the propeller. This produces directed air circulation and excellent mixing.

The propeller is preferably located symmetrically below the bottom and the measuring container such that the axis of rotation of the propeller is coaxial with the central axis of the outer housing.

To prevent contact between the drive motor of the propeller (preferably a conventional electromotor) and the air, which can be as hot as 500° C., the drive motor is disposed outside and preferably below the space containing the gas flow, and an output shaft of the drive motor penetrates through a wall of the outer housing or of the support in a sealed fashion. As an alternative, contactless magnetic transmission of the drive motion from the drive motor through the wall to the propeller is also possible.

The air can be heated external to the outer housing and that externally heated air can be supplied to the outer housing as well as discharged to the external temperature-controlling or heating device as required. However, the temperature-controlling device or heating device is preferably disposed in the outer annular chamber. The temperature-controlling device can e.g. be a heating and/or cooling coil which is disposed on the outside of the guiding wall. The coil can either be a tube containing a warm or cold fluid flow, or alternatively, the temperature-controlling device can comprise a resistive wire to heat the gas.

Circulation of the gas within the outer housing can be effected in a closed system. However, the outer housing preferably contains at least one connection for supplying and discharging the gas such that the gas can be discharged in response to thermal expansion. Cooler gas can be supplied from the outside to cool the measuring container to a desired temperature.

Further details and features of the invention can be extracted form the following description of an embodiment with reference to the drawing.

DESCRIPTION OF THE PREFERRED EMBODIMENT

Figure 1:
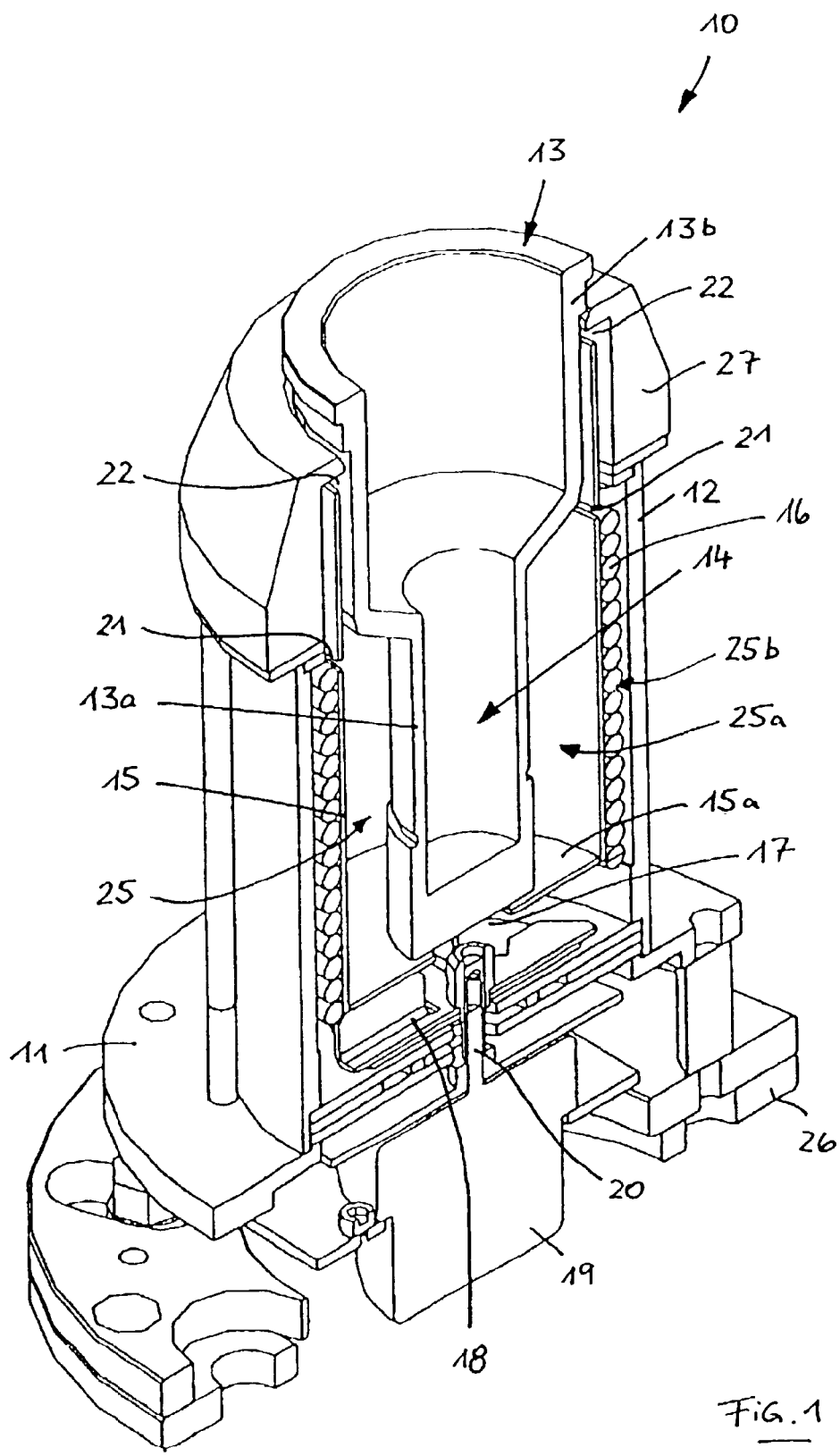
FIG. 1 shows a perspective sectional drawing of an inventive rotational rheometer.
Figure 2:
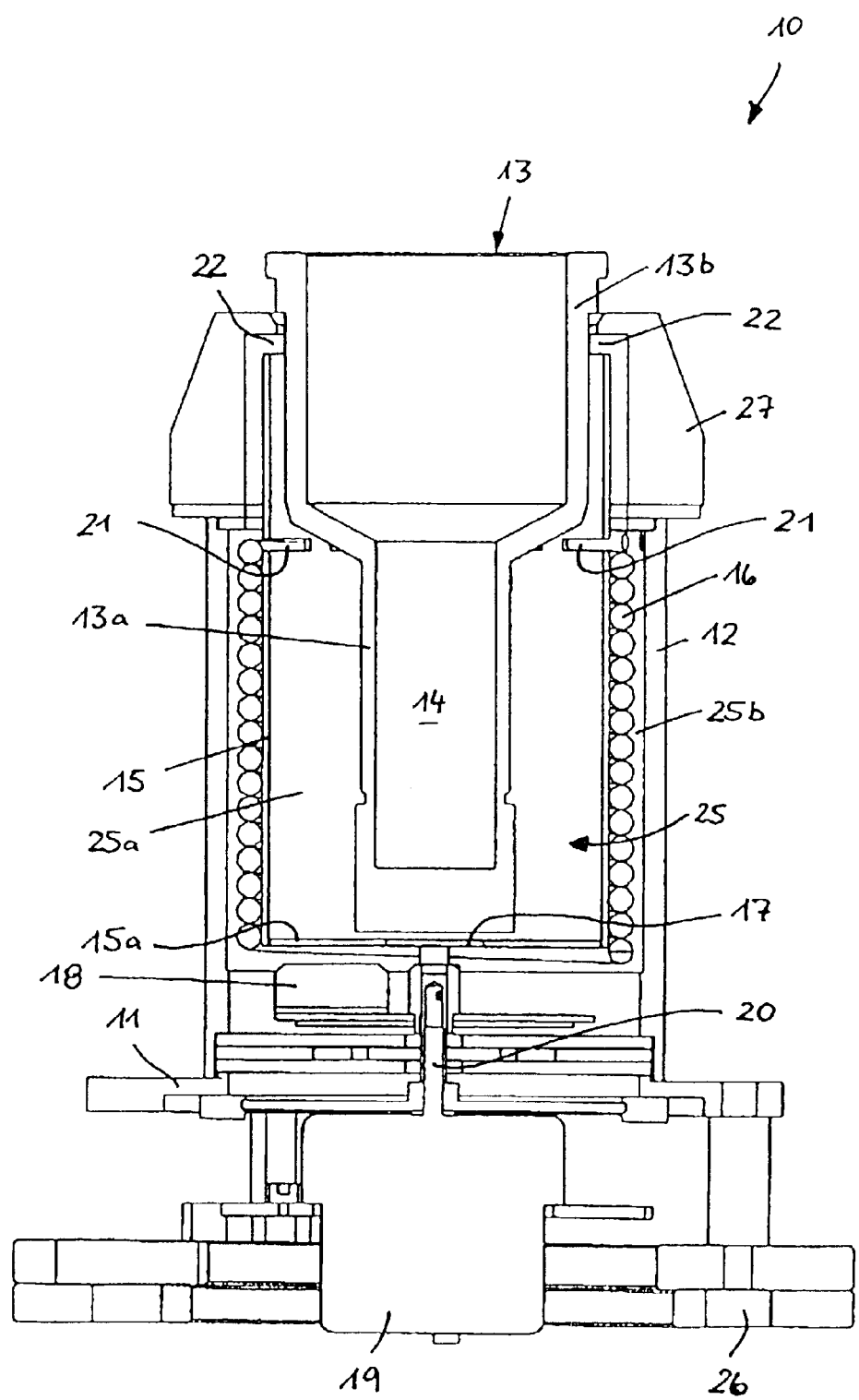
FIG. 2 shows a side, planar view of the section according to FIG. 1.
Figure 3:
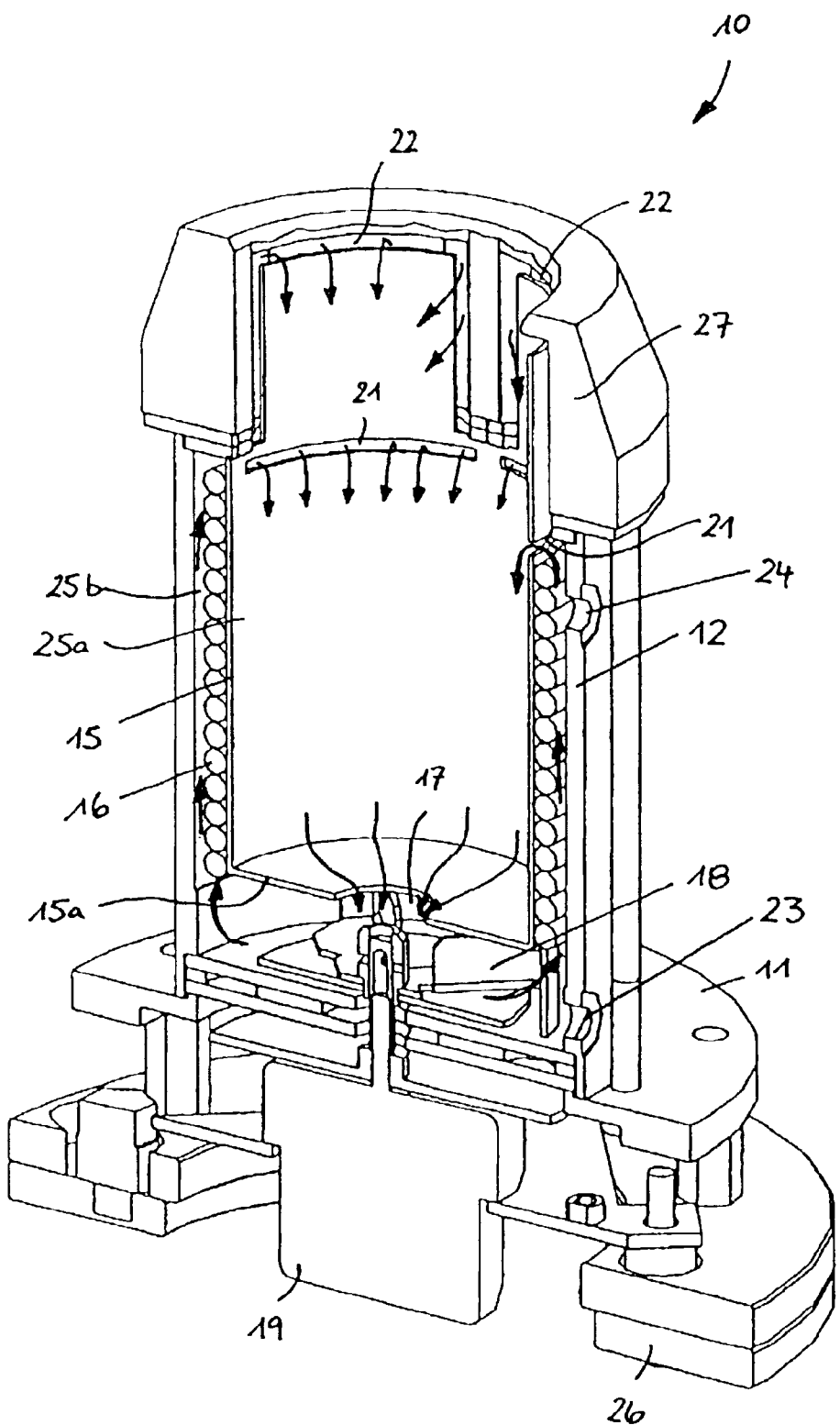
FIG. 3 shows a perspective sectional drawing of the rheometer in accordance with FIG. 1, without the measuring container.

The rotational rheometer 10 shown in FIGS. 1 through 3 has a base 26 which can be disposed on a support surface and whose upper side has a plate-like support 11. A circular cylindrical outer housing 12 is mounted to the support 11 whose upper end has an annular head 27. A stepped cylindrical measuring container 13 can be inserted from above into the inside of the outer housing 12. The lower cylindrical section 13a of the measuring container 13, which extends coaxially to the outer housing 12, has a measuring chamber 14. A cylindrical bearing section 13b, which is adapted to the inner dimensions of the annular head 27, is formed on the upper end of the measuring container 13 for supporting the inserted measuring container 13 on the annular head 27.

An annular space 25 is formed between the outside of the lower cylindrical section 13a of the measuring container 13 and the outer housing 12. A circular cylindrical guiding wall 15 is disposed within this annular space 25 and extends at a separation from the outer housing 12 and at a separation from the section 13a of the measuring container 13. In this fashion, the annular space 25 is subdivided into an inner annular chamber 25a and an outer annular chamber 25b. The lower end of the guiding wall 15 has a substantially horizontal bottom 15a which has a central opening 17 disposed below the lower end of the measuring container 13. The outer surface of the guiding wall 15 has a temperature-controlling device in the form of a heating coil 16. As shown in particular in FIG. 3, several openings 21 or gaps 22 are provided in the upper region of the guiding wall 15 to provide a fluid connection between the outer annular chamber 25b and the inner annular chamber 25a.

A propeller 18 is provided below the bottom 15a, inside of the outer housing 12. The propeller 18 can be rotated about a vertical axis of rotation and has a drive motor 19 which is mounted below the support 11 and has a drive shaft 20 penetrating through that support 11. The drive shaft 20 can be disposed in the support 11 in a fluid-tight fashion and/or the drive motor 19 can be thermally shielded from the propeller around which the temperature-controlling gas flows.

FIG. 3 shows that a first connection 23 for supplying or discharging air is provided in the lower region of the outer housing 12. A similar further connection 24 is formed in the upper region of the outer housing 12 close to the upper end of the heating coil 16.

During operation of the rotational rheometer 10, a sample material is introduced into the measuring chamber 14 of the measuring container 13. A circular cylindrical rotor is also introduced into the measuring chamber 14 in a conventional fashion (not shown) for exerting shearing forces on the sample material. At the same time, the heating coil 16 is activated and the propeller 18 is rotated, wherein the propeller 18 forces the air below the bottom 15a radially outwardly to rise in the outer annular chamber 25b along the heating coil 16 as indicated by the arrows in FIG. 3. The air is thereby heated and then enters at the upper region of the outer annular chamber 25b through the openings 21 and the gaps 22 into the inner annular chamber 25a and flows therein downwardly towards the bottom 15a to heat the outside of the lower cylindrical section 13a of the measuring container 13 and therefore the sample material located in the measuring chamber 14. As indicated by arrows in FIG. 3, the air flows in the lower region of the separating wall 15 through the central opening 17 of the bottom 15a and returns to the propeller 18.

When the connections 23 and 24 are closed, the air can be circulated within the outer housing 12 as indicated above.

We claim:

1. A rotational rheometer having circulating gas for temperature-control of a sample material during measurements of rheological values thereof, the rheometer comprising:

a support;

a substantially cylindrical outer housing seating on said support;

a measuring container inserted into said outer housing in a substantially coaxial manner to define a radial annular space between said outer housing and said measuring container, the measuring container having a measuring chamber for receiving the sample material;

a circulating device disposed within said outer housing, said circulating device for circulating the gas through said annular space to temperature-Control an outside of said measuring container and the sample material contained therein; and a cylindrical guiding wall disposed within said annular space at a separation from and coaxially to said outer housing to subdivide said annular space into an inner annular chamber and an outer annular chamber, wherein said outer annular chamber and said inner annular chamber communicate via at least one opening in said guiding wall.

2. The rotational rheometer of claim 1, wherein said circulating device comprises a propeller with rotational drive.

3. The rotational rheometer of claim 2, wherein said propeller has an axis of rotation extending coaxially to a central axis of said outer housing.

4. The rotational rheometer of claim 2, wherein said rotational drive comprises a motor for driving said propeller, said drive motor disposed below a space through which the gas flows, said drive motor having a output shaft connected to said propeller, said output shaft penetrating through a wall of said support in a sealed fashion.

5. The rotational rheometer of claim 1, wherein said guiding wall has a bottom disposed below the measuring container, said bottom having at least one opening.

6. The rotational rheometer of claim 5, wherein said circulating device is disposed below said bottom.

7. The rotational rheometer of claim 1, further comprising a temperature-controlling device, said temperature-controlling device disposed in said outer annular chamber.

8. The rotational rheometer of claim 7, wherein said temperature-controlling device is a heating device for gas.

9. The rotational rheometer of claim 7, wherein said temperature-controlling device comprises a coil seating on an outside of said guiding wall for at least one of heating and cooling.

10. The rotational rheometer of claim 7, wherein temperature-controlling device comprises a resistive wire.

11. The rotational rheometer of claim 1, wherein said outer housing has least one connection for supplying and discharging the gas.

* * * * *